(12) United States Patent
Rogalski

(10) Patent No.: US 6,712,854 B2
(45) Date of Patent: Mar. 30, 2004

(54) ACROMIAL-HUMERAL PROSTHESIS AND METHOD OF IMPLANTATION

(76) Inventor: Roger A Rogalski, 935 Wintergreen Ave., Gardnerville, NV (US) 89410

( * ) Notice: Subject to any disclaimer, the term of this patent is extended or adjusted under 35 U.S.C. 154(b) by 74 days.

(21) Appl. No.: 10/054,989

(22) Filed: Jan. 25, 2002

(65) Prior Publication Data

US 2003/0144738 A1 Jul. 31, 2003

(51) Int. Cl.[7] ................................................. A61F 2/40
(52) U.S. Cl. .................................. 623/19.11; 623/19.14
(58) Field of Search ........................... 623/18.11, 19.11, 623/19.13, 19.14, 23.5, 23.53, 23.55, 23.58, 23.76

(56) References Cited

U.S. PATENT DOCUMENTS

| | | |
|---|---|---|
| 3,979,778 A | 9/1976 | Stroot |
| 4,550,450 A | 11/1985 | Kinnett |
| 4,990,161 A | 2/1991 | Kampner |
| 5,032,132 A | 7/1991 | Matsen, et al. |
| 5,080,673 A | 1/1992 | Burkhead, et al. |
| 5,593,448 A | 1/1997 | Dong |
| 5,944,757 A | 8/1999 | Grammont |
| 2002/0183858 A1 * | 12/2002 | Contiliano et al. ...... 623/23.76 |

\* cited by examiner

Primary Examiner—Eduardo C. Robert
Assistant Examiner—Anuradha Ramana
(74) Attorney, Agent, or Firm—Siemens Patent Services, LC

(57) ABSTRACT

The present invention features an acromial-humeral prosthesis for use in performing acromial-humeral arthoplasty. The prosthesis is useful for cases where massive, irreparable tears to the rotator cuff have occurred. The principle function of the prosthesis is to prevent superior migration of the humeral head. An acromial tray is inserted using a specialized insertion tool. The acromial tray is held in place against a prepared inferior surface of the acromion by a pair of screws. A concave, disc-like polymeric component is affixed to the bottom of the acromial tray by sliding the component onto one or more matching rails on the inferior surface of the acromial tray This component is relieved to accept the long head of the biceps tendon anteriorly and the greater trochanter laterally. The inventive prosthesis helps prevent non-anatomical articulations of the humerus and other inappropriate glenohumeral kinematics.

19 Claims, 4 Drawing Sheets

ACROMIAL-HUMERAL PROSTHESIS AND METHOD OF IMPLANTATION

BACKGROUND OF THE INVENTION

1. Field of the Invention

The present invention relates to a acromial-humeral prosthesis, and more particularly, to a acromial-humeral prosthesis for use in preventing superior migration of the humeral head after massive rotator cuff tears while helping retard rotator cuff arthropathy.

2. Description of the Prior Art

The loss of integrity of the rotator cuff muscle/ligament group often results in pain, generally due to superior migration of the humeral head causing non-anatomical articulation with the inferior surface of the acromion, as well as other inappropriate gleno-humeral kinematics. These losses of cuff integrity are generally caused by massive, irreparable tears of the rotator cuff. Following such tears, secondary development of cuff arthropathy often follows.

Presently, surgical corrective techniques include a massive debridement, typically including excising back the torn, irreparable portions of the cuff as well as any associated inflammatory bursitis. These procedures then often include sub-acromial decompression and distal clavicle resection. Such procedures, intended primarily for pain relief, do not address the mechanical abnormalities associated with torn rotator cuffs. Rarely, after such a procedure, is there any improvement in function. In addition, the results of such procedures typically have unpredictable, mixed outcomes.

Another approach to the torn rotator cuff problem is to perform an over-sized humeral hemi-arthroplasty. Like the debridement procedure, these procedures do not address the abnormal mechanics associated with an incompetent rotator cuff and the consequent potential superior migration of the prosthetic head through the tear. Total constrained or unconstrained shoulder replacements are also used to treat irreparable rotator cuff tears.

Other surgical techniques such as allograft tissue or transfer of local autogenous tissue to the affected area have also not proven to be reliable surgical techniques.

Such prior art techniques are taught in several United States patents.

U.S. Pat. No. 3,979,778, for SHOULDER PROSTHESIS, issued Sep. 14, 1976, to Jerome H. Stroot teaches a two-component (i.e., a humeral and a glenoid component) prosthesis having spherical articulation thereby allowing a relatively wide range of joint movement. In addition, a novel humeral component may be used alone as a partial prosthesis. However, STROOT does not address a torn rotator cuff.

U.S. Pat. No. 4,550,450, for TOTAL SHOULDER PROSTHESIS SYSTEM, issued Nov. 5, 1985, to James G. Kinnett, teaches a three-component prosthesis. In addition the traditional humeral and glenoid components, a third, acromial component is added to replace the acromial-clavicular articulation which, helps prevent superior displacement of the humerus.

U.S. Pat. No. 4,990,161, for IMPLANT WITH RESORBABLE STEM, issued Feb. 5, 1991, to Stanley L. Kampner teaches a joint prosthesis suitable for knee, finger, hip or shoulder implantation, the prosthesis having a biodegradable anchor pin.

U.S. Pat. No. 5,032,132, for GLENOID COMPONENT, issued Jul. 16, 1991, to Frederick A. Matsen, III, et al. teaches a glenoid component for shoulder arthoplasty. The component is attached to the scaplua by anchor pins.

U.S. Pat. No. 5,080,673, for GLENOID PROSTHESIS AND METHOD OF USE, issued Jan. 14, 1992, to Walter Z. Burkhead, et al., teaches another pin-attached glenoid component for use in shoulder arthoplasty. Detailed steps of a method for attaching the component are provided.

U.S. Pat. No. 5,593,448, for GLENOID COMPONENT FOR SHOULDER PROSTHESIS AND IMPLANT METHOD, issued Jan. 14, 1997, to Nicholas N. G. Dong teaches a glenoid component utilizing a series of pins for securing the component to the scaplua. A method for implanting the glenoid component is also provided.

U.S. Pat. No. 5,944,757, for TOTAL TROCHITERO-ACROMIAL SHOULDER PROSTHESIS, issued Aug. 31, 1999, to Paul Marie Grammont teaches a one-piece, sub-acromial element adapted for interaction with a trochiterian element. The acromial element is cemented to the inferior surface of an acromion after it has been appropriately sectioned. The trochiterian element has a substantially spherical shape and is composed of high-density polyethylene.

The prosthesis of the present invention differs substantially from that of GRAMMONT. First, the inventive prosthesis consists only of a acromial element. The two-piece construction of the inventive acromial element allows for a metallic backed component to encourage bone growth and a modular polymeric lower portion optimized for articulation with the humeral head, not a trochiterian element as taught by GRAMMONT. The inventive prosthesis eliminates the need for a trochiterian element by specially engineering the polyethylene component to accept the humeral head directly. By molding the polyethylene in the appropriate shape the polyethylene component can eliminate the entire need of any additional component. The inventive acromial element is affixed to the acromion by porous ingrowth backing and supplemental screw fixation, not cement.

None of the aforementioned United States patents teach or suggest an apparatus or method similar to that of the present invention. The subject matter of each of these patents is directed to glenoid and/or humeral components for use in a shoulder joint prosthesis and not to a acromial-humeral prosthesis intended to control superior migration of the humeral head after a massive, irreparable rotator cuff tear.

None of the above inventions and patents, taken either singly or in combination, is, however, seen to anticipate or suggest the instant invention as claimed.

SUMMARY OF THE INVENTION

The present invention relates to a acromial-humeral prosthesis for use in performing acromial-humeral arthoplasty. The prosthesis is useful for cases where massive, irreparable tears to the rotator cuff have occurred. The principle function of the inventive prosthesis is to provide pain relief by preventing superior migration of the humeral head. A metal, porous coated acromial tray is inserted using an insertion tool using a typical anterior, anterior-lateral or mini-lateral surgical approach. The acromial tray is held in place against a prepared inferior surface of the acromion by a pair of trans-acromial screws inserted from above the acromion. A concave, disc-like component, typically made from ultra high density polyethylene, is affixed to the bottom of the acromial tray by sliding the component onto one or more matching rails on the inferior surface of the acromial tray. Other methods of fixation of the polyethylene component to the metal tray could be envisioned. This component, designed for direct articulation with the humeral head, is relieved to accept the long head of the biceps tendon (if intact) anteriorly and the greater trochanter laterally. An insertion tool adapted for implantation of the prosthesis as well as other tools such as a drill guide are also provided. The inventive prosthesis helps prevent non-anatomical articulations of the humerus and other inappropriate gleno-humeral kinematics. In addition, secondary development of rotator cuff arthropathy is minimized. The inventive prosthesis also increases tension on associated shoulder musculature, resulting in increased strength and range of motion.

Accordingly, it is a principal object of the invention to provide a humeral-acromial prosthesis for use in patients having massive, irreparable rotator cuff tears.

It is another object of the invention to provide a humeral-acromial prosthesis which provides pain relief in patients having massive, irreparable rotator cuff tears.

It is a further object of the invention to provide a humeral-acromial prosthesis which may easily be implanted using either arthroscopically assisted or open surgical techniques.

Still another object of the invention is to provide a humeral-acromial prosthesis which is formed from an acromial tray having a porous surface for fixation against the inferior surface of a prepared acromion, and a concave, polymer disk shaped component for attachment to the inferior surface of the acromial tray.

An additional object of the invention is to provide a humeral-acromial prosthesis wherein the polymer component is anatomically shaped for direct articulation with the humeral head.

It is again an object of the invention to provide a humeral-acromial prosthesis wherein the polymer component attached to the acromial tray is shaped to provide anterior passage for the head of the biceps tendon, if intact.

It is a still further object of the invention to provide a humeral-acromial prosthesis wherein the polymer component attached to the acromial tray is shaped to provide lateral passage for the greater trochanter.

It is an additional object of the invention to provide a humeral-acromial prosthesis which is affixed to the acromion using a pair of trans-acromial screws with the potential for biological in-growth onto the porous tray.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

The present invention relates to a humeral-acromial prosthesis.

Figure 1A:
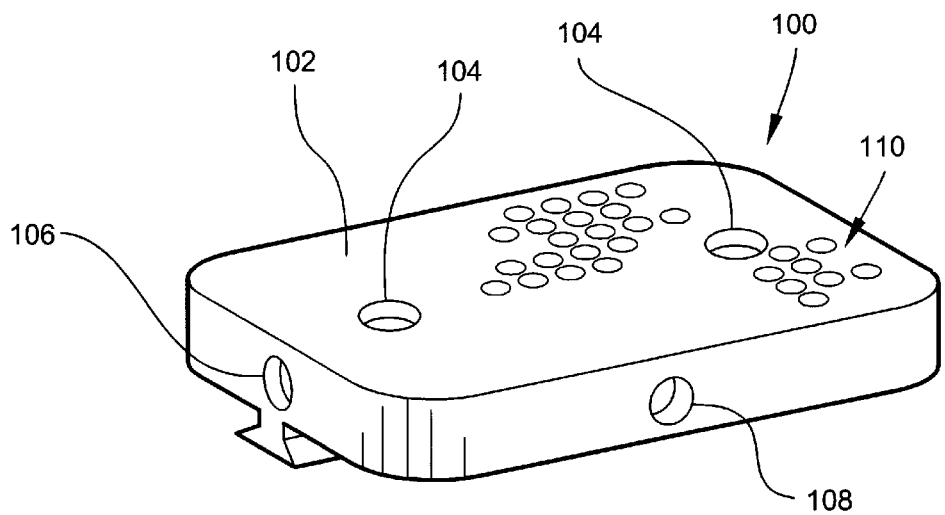
FIGS. 1a and 1b are perspective and end elevational views, respectively, of the acromial tray portion of the inventive prosthesis.
Figure 1B:
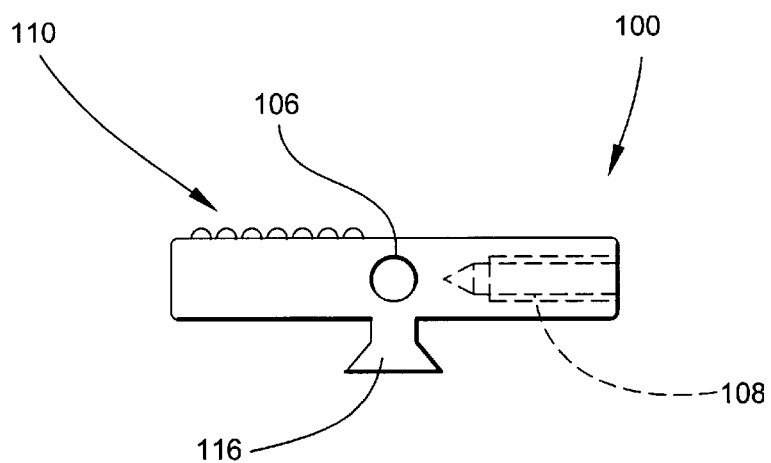

Referring first to FIGS. 1a and 1b, there are shown prospective and end-elevational views of the acromial tray portion of the inventive prosthesis, generally at reference number 100. Acromial tray 100 is typically made from titanium, chrome cobalt molybdenum, stainless steel or other similar materials such as are well known to those skilled in the orthopedic surgical art. A ceramic coating may be applied to the superior surface of acromial tray 100 to provide a surface conducive to bone grown into the surface. Any material possessing sufficient strength and having the ability to encourages porous bone growth into the porous, superior surface of acromial tray 100 could be used. A pair of threaded holes 104 are provided in the superior surface 102 of acromial tray 100. Holes 104 accept cancellous screws 112 (FIG. 3) and act as anchoring means. A threaded hole 105, adapted to receive the distal end of insertion tool 114 (FIG. 3), is placed in a lateral end of acromial tray 100. Hole 106 is used when the prosthesis, including acromial tray 100 is to be implanted using a lateral surgical approach. A second, similar hole 108 is also provided in tbe anterior side of acromial tray 100 for interaction with insertion tool 114 when the prosthesis is implanted using an anterior-lateral surgical approach. Hole 108 is angled to properly align insertion tool 114 when an anterior-lateral insertion is performed. Holes 106 and 108 serve as means for removably attaching an insertion tool. Raised beads or other similar structures 110 on the superior surface of acromial tray 100 are provided to promote porous bone growth into scrotal tray 100. Other techniques for roughening superior surface 102 known to those skilled in the art could also be used to prepare superior surface 102 to facilitate bone growth. First attachment means, in the form of track 116 on the inferior surface of acromial tray 100 is provided to attach the polymeric component 120 (FIG. 2) to the inferior surface of acromial tray 100. It will also be obvious that track 116 could have a number of different Cross sectional shapes other than the shape shown for purposes of disclosure. It should also be obvious that more than one track could be provided.

It will be recognized that other component shape, for example, more discoid shapes with varied widths, lengths, and sizes could be used to meet varying anatomical or individual pathology requirements could be used. The invention is not, therefor, considered limited to the specific shapes chosen for purposes of disclosure.

Figure 2:
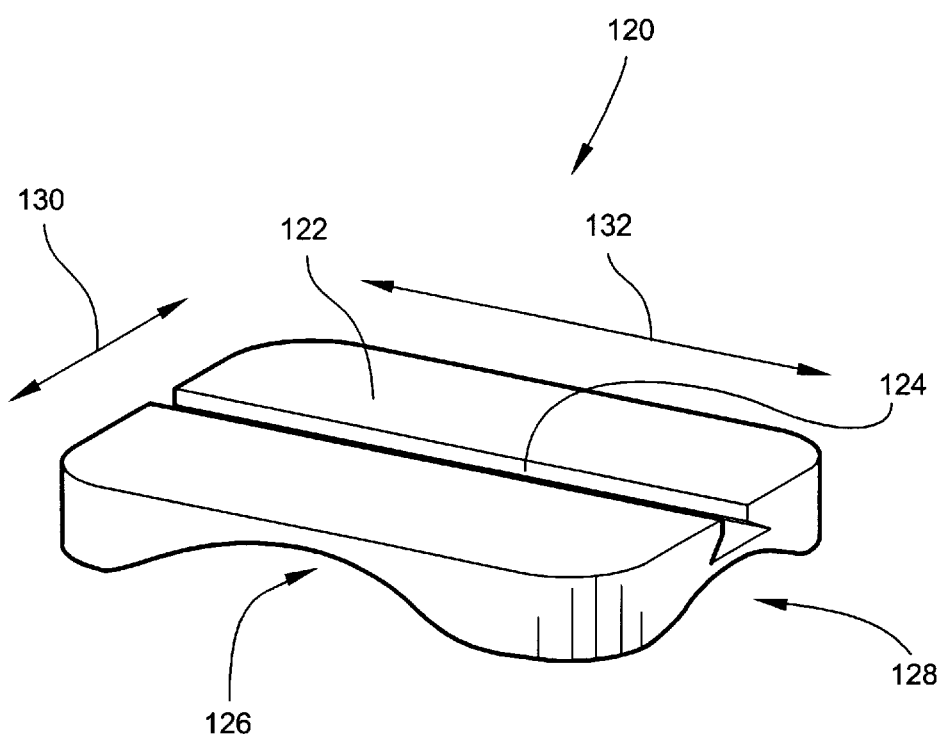
FIG. 2 is a anterior perspective view of the polymeric component of the prosthesis of the invention.
Figure 3:
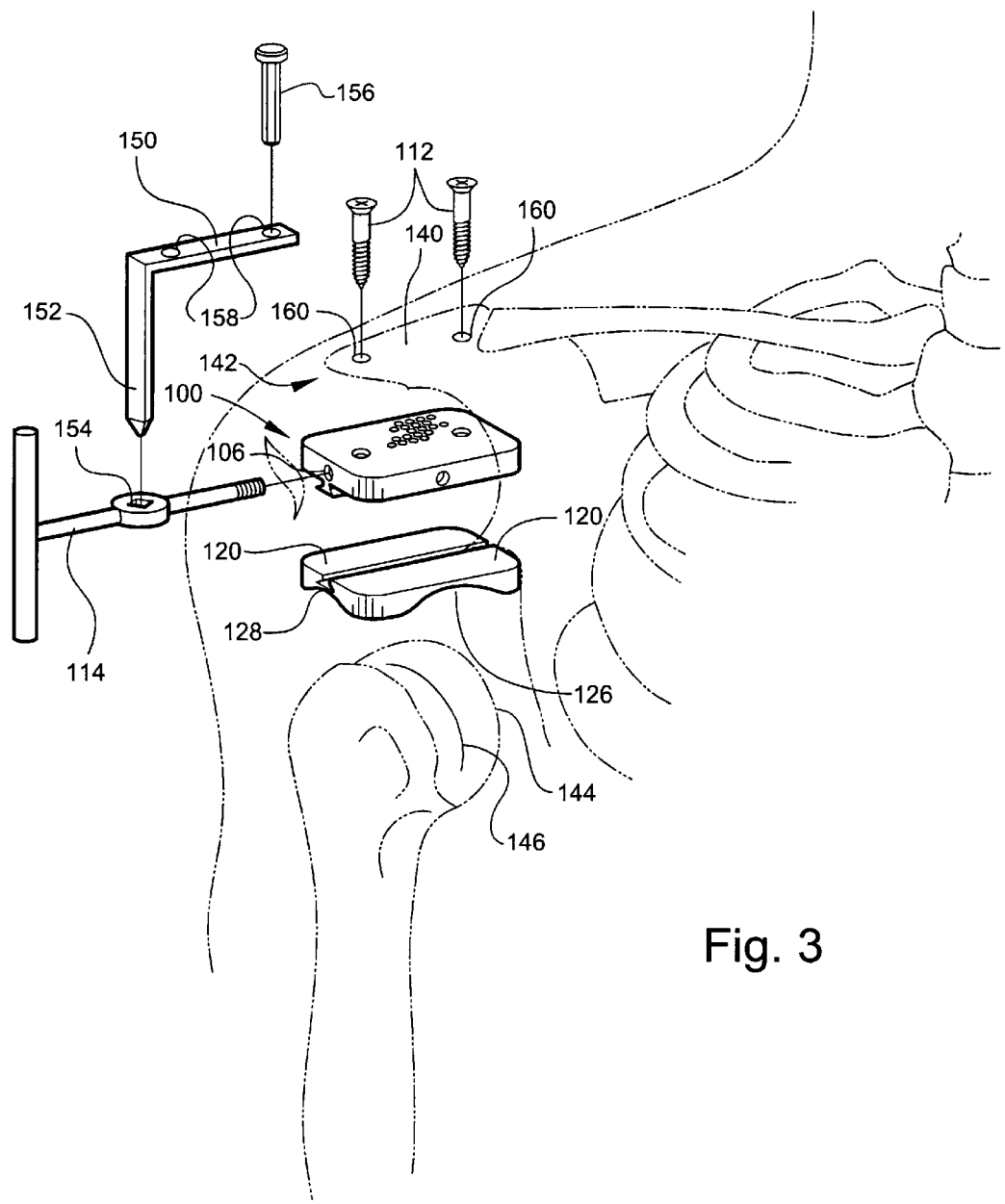
FIG. 3 is an exploded, anterior schematic view of the shoulder region of a human showing the inventive prosthesis components and the associated assembly tools in their approximate operable positions.

Referring next to FIG. 2, there is shown an anterior perspective view of the second component of the inventive prosthesis, 120. This component has a concave inferior surface (not shown) adapted for interaction with the humeral head 144 (FIG. 3). Component 120 is typically made from cross-linked, ultra high density polyethylene, but other suitable materials could, of course, be substituted. Secondary attachment means, in the form of groove 124 is provided in superior surface 122 of component 120, groove 124 being adapted to interact closely with track 116 (FIG. 1b) to slidably secure component 120 to acromial tray 100. A first groove 126 of essentially semi-circular shape is provided along the inferior surface of component 120 along an anterior-posterior axis 130. Groove 126 allows the normal passage of the head of the biceps tendon 146 (FIG. 3) to pass unimpeded between humeral head 144 and the inferior sur face of component 120, Likewise, a second groove 126 in the inferior surface of component 120 along lateral axis 132 allows the free excursion of the greater trochanter (riot shown) during abduction and forward flexion of the humorous. Both grooves 126 and 128 are formed anatomically correctly to properly receive, respectively the biceps tendon 146 and the greater trochanter (not shown).

Referring now to FIG. 3, there is shown an exploded anterior schematic view of the shoulder portion of a human torso with the inventive prosthesis inserted along with the necessary insertion tools used to implant the prosthesis. Acromial tray 100 is shown below the inferior surface 142 of acromion 140. Inferior surface 142 is assumed to have been prepared according to standard and well known sub-acromial decompression procedures. Such procedures may be performed either arthroscopically or by using an open procedure. This sub-acromial perpetration may have previously been performed or, alternatively, may be performed at the time of the insertion of the inventive prosthesis.

Insertion tool 114 is shown detached from acromial tray 100 but positioned for interaction with hole 106 for a lateral procedure. An aiming guide 150 having an attachment stem 152 is shown above insertion tool 114. A socket 154 on insertion tool 114 is adapted to receive stem 152 of aiming guide 150. An insertion tool 114 having a T-shaped handle has been shown for purposes of disclosure. However, other handle shapes could easily be used. The interconnection of stem 152 with socket 154 allows the holes 158 in aiming guide 150, correspond to holes 104 in acromial tray 100 and must be precisely aligned with holes 104 when acromial tray 100 is properly seated against the acromion 140. Once in place, drill guides 156 may be inserted in holes 158 and trans-acromial holes 160 may be accurately drilled using surgical drilling techniques well known to those skilled in the orthopedic surgical arts. Once trans-acromial holes 160 have been drilled, acromial tray 100 may be secured to inferior surface 142 by cancellous screws 112. Once acromial tray 100 is securely in place, component 120 may be slid onto rail 116.

Figure 4:
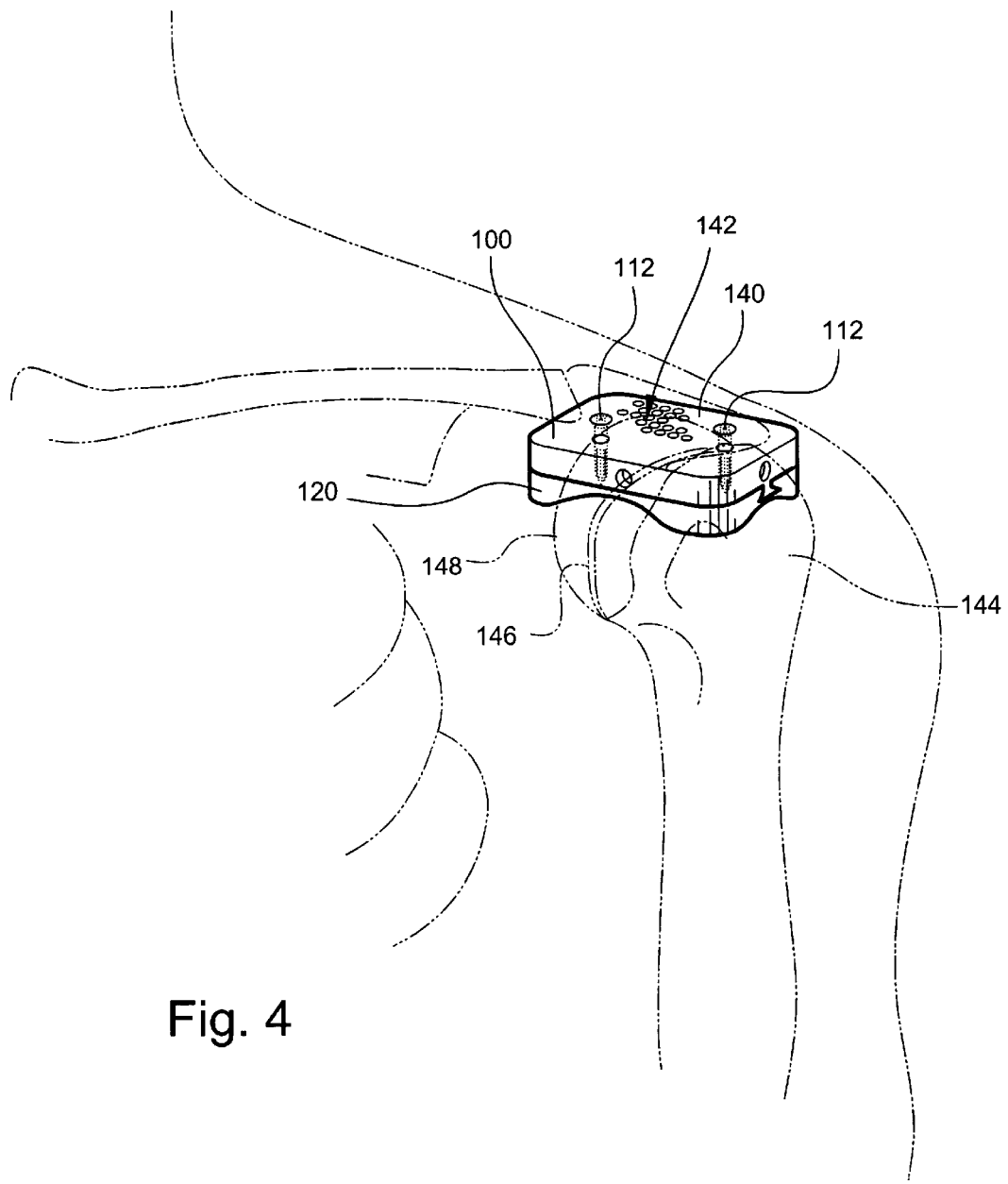
FIG. 4 is an anterior view showing the inventive prosthesis in place in the shoulder of a patient.

Referring now to FIG. 4, there is shown an anterior view of the glenoid-humeral joint with the prosthesis of the present invention in place. Humeral head 144 articulates with the glenoid cavity 148 of the scapula as well as with polymer component 120 mounted by means of acromial tray 100 against the inferior surface 142 of the acromion 140 by trans-acromial screws 112. Groove 126 in the inferior surface of polymer component 120 allows passage of biceps 146 (if present).

Refer again to FIG. 3. In use, the prosthesis of the invention is implanted in a patient by first preparing the inferior surface 142 of acromion 140. The preparation consists of debriding inferior surface 142 with a burr or saw to a flat surface, removing all anterior and lateral osteophytes. This decompression should be conservative thereby leaving adequate thickness in the acromion 140 to support the prosthesis. However, the decompression should be sufficient to ensure that there is an exposed surface of cancellous bone on inferior acromial surface 142. The preparation may ether be done in a separate procedure, or alternately, be performed at the same time the prosthesis is to be inserted. The decompression procedure may be performed either arthroscopically or using an open technique. These decompression procedures are well known to those skilled in the orthopedic surgical art and per se, forms no part of the present invention.

The prosthesis may be inserted using either of two approaches to the sub-acromial space: a lateral or antero-lateral procedure as best suits an individual case. An appropriate incision is first made. If a lateral insertion is being performed, the deltoid muscle group must be split to allow passage of the prosthesis components (i.e. acromial tray 100 and polymer component 120). If an antero-lateral approach is utilized, the anterior deltoid must be taken down. Insertion tool 114 is screwed in the appropriate hole 106, (for lateral approach) or 108 (for antero-lateral approach) on acromial tray 100. Insertion tool 114 is used both to propel and guide acromial tray 100 as it is passed into the sub-acromial space through the incision. Once in place, stem 152 of aiming tool 150 is inserted into socket 154 of insertion tool 114. Aiming tool 150 is now accurately positioned to act as a drill template. Drill guides 156 are next inserted in holes 158 of aiming tool 150. Once in place, two trans-acromial holes are drilled using well known surgical apparatus and techniques. Drill guides 156 are removed and cancellous, trans-acromial screws 112 are inserted from a superior position into threaded holes 104 in the superior, beaded surface of acromial tray 100. Once screws 112 are sufficiently tightened, the superior, beaded surface of acromial tray 100 is secured in intimate contact with inferior surface 142 of the acromion 140.

The textured (i.e., beaded) superior surface 102 of acromial tray 100 promotes cancellous bone growth from inferior surface 142 into the spaces between the beads, thereby, with time, forming a cemented bond between inferior surface 142 and the superior surface of acromial tray 100.

It is to be understood that the present invention is not limited to the embodiments described above, but encompasses any and all embodiments within the scope of the following claims.

What is claimed is:

1. An acromial prosthesis system, comprising:
   an acromial tray having a superior surface, an inferior surface, opposing lateral edges, an anterior edge and a posterior edge;
   said acromial tray having at least two threaded, screw-receiving holes disposed at a predetermined spacing in a central region of said superior surface; at least one rail disposed on said inferior surface to slidably receive and retain a polymeric component adjacent said inferior surface;
   said acromial tray further comprising means for removably attaching an insertion tool;
   a polymeric component having a superior surface, an inferior surface, an anterior edge, a posterior edge and opposing lateral edges, said superior surface comprising at least one groove adapted for slidable interaction with said at least one rail, said inferior surface being substantially concave and adapted for articulate interaction with the head of a humerus;
   whereby superior migration of said head of said humerus is minimited during abduction and forward flexion of said humerus.

2. The acromial prosthesis system as recited in claim 1, further comprising an insertion tool, said insertion tool comprising a substantially T-shaped handle with a shaft rigidly attached thereto, said shaft having a distal end adapted for removable interaction with said means for removably attaching an insertion tool of said acromial tray, said insertion tool further comprising a socket on said shaft a predetermined distance from said distal end, said socket being adapted to removably receive an aiming tool.

3. The scrotal prosthesis system as recited in claim 2, further comprising an aiming tool, said aiming tool comprising a substantially L-shaped structure, a first lag of said L-shaped structure comprising a shaft adapted for removable insertion into said socket, the second leg of said L-shaped structure comprising an elongate, planar member having at least two spaced-apart holes therethrough, said at least two holes being spaced at a distance one from another substantially equal to said predetermined spacing of said at least two threaded, Screw-receiving holes in said acromial tray, and at a predetermined distance from said distal end of said shaft of said insertion tool.

4. The acromial prosthesis system as recited in claim 1, wherein said means for removably attaching an insertion tool comprises at least one threaded attachment hole disposed in at Least one of said lateral edges, said anterior edge and said posterior edge of said acromial tray.

5. The acromial prosthesis system as recited in claim 4, wherein said at least one threaded attachment hole is disposed substantially perpendicularly to at least one of said lateral edges, said anterior edge and said posterior edge of said acromial tray.

6. The acromial prosthesis system as recited in claim 4, wherein said at least one threaded attachment hole is disposed at an angle relative to at least one of said lateral edges, said anterior edge and said posterior edge of said acromial tray.

7. The acromial prosthesis system as recited in claim 4, wherein said at least one threaded attachment hole comprises a mirrored pair of threaded attachment holes disposed in opposing ones of said edges of said acromial tray to allow interchangeable use of said acromial tray on a left acromion or a right acromion of a recipient of said prosthesis system.

8. The acromial prosthesis system as recited in claim 1, wherein said interior, substantially concave surface further comprises at least one of the group: a groove along an anterior-posterior axis adapted to receive a biceps tendon and a groove along a lateral axis for receiving a greater trochanter muscle group.

9. A method for inserting an acromial prosthesis, the steps comprising:
   providing a two-piece acromial-humeral prosthesis comprising: an acromial tray structure having a textured superior surface, at least one threaded hole adapted to receive and secure a trans-acromial screw, and means for removably attaching an insertion tool; a polymer component adapted for slidable attachment to said inferior surface of said acromial tray;
   making an incision proximate the sub-acromial region of a recipient;
   attaching an insertion tool to said, insertion tool attachment means of said acromial tray;
   inserting said acromial tray into said sub-acromial region through said incision to a sub-acromial position and temporarily securing said acromial tray in said sub-acromial position;
   operatively attaching an aiming tool to said insertion tool, said aiming tool comprising drill guides;
   drilling at least one trans-acromial hole aligned with said at least one threaded hole in said superior surface of said acromial tray;
   inserting at least one trans-acromial screw from a superior surface of said acromion into said at least one threaded hole in said superior surface of said acromial tray; and
   tightening said at least one trans-acromial screw to a predetermined tightness.

10. The method for inserting an acromial prosthesis as recited in claim 9, the steps further comprising:
    performing a sub-acromial decompression prior to said inserting step (d).

11. The method for inserting an acromial prosthesis as recited in claim 9, wherein said polymer component comprises a substantially concave inferior surface adapted for articulate interaction with the head of a humerus.

12. The method for inserting an acromial prosthesis as recited in claim 11, wherein said inferior surface of said polymer component further comprises a substantially concave inferior surface adapted for articulate interaction with the head of a humerus.

13. The method for inserting an acromial prosthesis as recited in claim 12, wherein said inferior, substantially concave surface further comprises at least one of the group: a groove along an anterior-posterior axis adapted to receive a biceps tendon and a groove along a lateral axis for receiving a greater trochanter muscle group.

14. An acromial replacement assembly for placement as a prosthestic shoulder implant, said assembly comprising:
    a tray element for attachment to an acromion, said tray element having an upper surface, a lower surface and side surfaces joining said upper and lower surfaces, said tray element further having
    anchoring means for attaching the tray element to the acromion,
    first attachment means for coupling to a humeral contact element; and
    a humeral contact element removably connected to said tray element,
    said humeral contact element having an upper and lower surface,
    secondary attachment means, located on said upper surface of said humeral contact element, for coupling to said first attachment means of said tray element; and
    means for removably attaching an insertion tool.

15. The acromial replacement assembly, as in claim 14, wherein said tray element further comprises means formed on said upper surface for promoting bone growth into said tray, said bone growth promoting means providing a roughened surface which facilitates bone coupling; and
    wherein said anchoring means, for coupling the tray element to the acromion, is formed on the upper surface of said tray element.

16. The acromial replacement assembly, as in claim 15 further comprising an insertion tool adapted for operative coupling to the means for removably attaching en insertion tool for surgically implanting said assembly; and
    wherein said receiving means are located on at least One side of the tray element.

17. The acromial replacement assembly, as in claim 16, wherein said first attachment means comprises a longitudinal protrusion located on the lower side of the tray element; and
    said secondary attachment means comprises a longitudinal recess, located on the upper surface of said humeral contact element, for slidably and removably coupling said humeral contact element to said tray element.

18. The acromial replacement assembly, as in claim 17, wherein said lower surface of said humeral contact element has a concave surface formed therein for rotational interaction with a humeral head.

19. The acromial replacement assembly, as in claim 16, further comprising aiming means,
    said aiming means having aiming guides for guiding placement of said anchoring means on said acromion; and
    said aiming guides formed in symmetrical coupling alignment with the anchoring means.

* * * * *